US006774242B1

(12) United States Patent
Barth et al.

(10) Patent No.: US 6,774,242 B1
(45) Date of Patent: Aug. 10, 2004

(54) METHOD FOR ARYLATING AZA-HETEROCYCLES WITH ACTIVATED AROMATIC COMPOUNDS IN THE PRESENCE OF CAESIUM CARBONATE

(75) Inventors: Hubert Barth, Emmendingen (DE); Klaus Steiner, Emmendingen (DE); Simon Schneider, Merzhausen (DE); Ulrich Bayer, Ulm (DE); Manfred Westermayer, Gundelfingen (DE); Ulrike Wolfsperger, Gundelfingen (DE); Hans-Jürgen Betche, Vörstetten (DE)

(73) Assignee: Goedecke GmbH (DE)

( * ) Notice: Subject to any disclaimer, the term of this patent is extended or adjusted under 35 U.S.C. 154(b) by 0 days.

(21) Appl. No.: 09/889,341

(22) PCT Filed: Feb. 25, 2000

(86) PCT No.: PCT/EP00/01574

§ 371 (c)(1),
(2), (4) Date: Feb. 7, 2002

(87) PCT Pub. No.: WO00/59883

PCT Pub. Date: Oct. 12, 2000

(30) Foreign Application Priority Data

Mar. 30, 1999  (DE) ......................................... 199 14 610

(51) Int. Cl.$^7$ .......................................... C07D 209/04
(52) U.S. Cl. ..................................................... 548/511
(58) Field of Search .............................. 548/511, 563, 548/346.1

(56) References Cited

U.S. PATENT DOCUMENTS 5,977,361 A * 11/1999 Hartwig et al. ............. 544/264

OTHER PUBLICATIONS

PCT International Search Report, PCT/EP00/01574.
Lee et al., "Facile Synthesis of Alkyl Phenyl Ethers Using Cesium Carbonate", *Synthetic Communications*, vol. 25, No. 9, 1995, pp 1367–1370.
Dinsmore and Zartman, "Arylmethanesulfonates are Convenient Latent Phenols in the Nucleophilic Aromatic Substitution Reaction", *Tetrahedron Letters*, vol. 40, No. 21, 1999, pp 3989–3990.

Wolfe and Buchwald, "Improved Functional Group Compatibility in the Palladium–Catalyzed Amination of Aryl Bromides", *Tetrahedron Letters*, vol. 38, No. 36, 1997, pp 6359–6362.
Flessner and Doye, "Cesium Carbonate: A Powerful Inorganic Base in Organic Synthesis", *J. Prakt. Chem.*, vol. 341, No. 2, 1999, pp 186–190.
Gale and Wilshire, "The Preparation of Sole Polymethine Astrazon Dyes", *Aust. J. Chem.*, vol. 23, 1970, pp 1063–1068.
Stabler and Jahangir, "Preparation on N–Arylated Heterocycles by Nucleophilic Aromatic Substitution", *Synthetic Communications*, vol. 24, No. 1, 1994, pp 123–129.
Smith and Sawyer, "A Novel and Selective Method for N–Arylation of Indoles Mediated by KF/Al2O3", *Tetrahedron Letters*, vol. 37, No. 3, 1996, pp 299–302.
Mann et al., "Palladium–Catalyzed C–N(sp$^2$) Bond Formation: N–Arylation of Aromatic and Unsaturated Nitrogen and the Reductive Elimination Chemistry of Palladium Azolyl and Methyleneamido Complexes", *J. Am. Chem. Soc.*, vol. 120, No. 4, 1998, pp 827–828.
Maiorana et al., "Aromatic Nucleophilic Substitution on Haloarene Chromium Tricarbonyl Complexes: Nild N–Arylation of Indoles", *Synthesis*, 1998, pp 735–738.
Park et al., "Synthesis and $^1$H–nmr and N–Arylated Nitrogen–Containing Aromatic Heterocycles", *Bulletin of Korean Chemical Society*, vol. 6, No. 3, 1985, pp 141–144.

* cited by examiner

Primary Examiner—Rita Desai
Assistant Examiner—Robert Shiao
(74) *Attorney, Agent, or Firm*—Charles W. Ashbrook; Matthew J. Russo

(57) ABSTRACT

The invention concerns a process for the preparation of N-aryl-aza-heterocycles of the general formula I

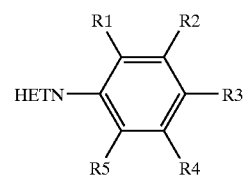

by reaction of aza-heterocycles with activated aryl halides with use of caesium carbonate without addition of further catalysts at room temperature.

5 Claims, No Drawings

METHOD FOR ARYLATING AZA-HETEROCYCLES WITH ACTIVATED AROMATIC COMPOUNDS IN THE PRESENCE OF CAESIUM CARBONATE

The subject of the invention is a process for the nucleophilic substitution on activated aromatics of the general formula XIV

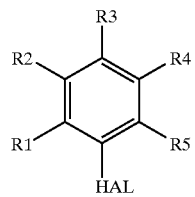

XIV in which R1, R2, R3, R4 and R5 are the same or different and signify a hydrogen atom, a nitro group, a cyano group, an alkoxycarbonyl group with up to 5 C-atoms, an aldehyde group, an alkylcarbonyl group with up to 5 C-atoms, an arylcarbonyl group or an amide group, whereby the radicals R1 to R5 cannot all simultaneously be a hydrogen atom and HAL stands for a halogen atom but especially for a fluorine atom, with nucleophils, such as alcohols, amines, sulphoximides, CH-acidic compounds of the formulae V to XI

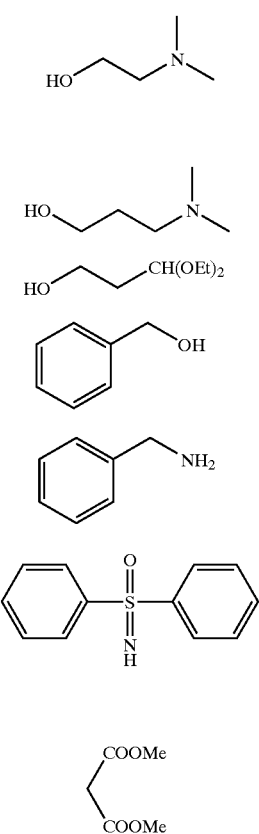

Figure 1 in dipolar aprotic solvents, especially dimethylformamide, with use of caesium. carbonate.

The process is preferred for the preparation of compounds of the general formula I

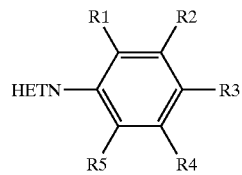

I in which HETN signifies an aromatic aza-heterocycle with, in all, 5 or 6 ring atoms, whereby up to 3 ring atoms can be nitrogen atoms, and up to two further aromatic carbon rings can be condensed on to the heterocycle and R1 to R5 have the above-mentioned meaning.

Compounds of the general formula I play an important part in medicinal chemistry. Thus, e.g. one finds the N-aryl-aza-heterocyclic structure in substances with anti-oestrogenic (E. Angerer, J. Strohmeier, J. Med. Chem. 30, 131, 1987), with analgesic (E. J. Glamkowski et al., J. Med. Chem. 28, 66, 1985), with anti-diabetic (R. B. Chapleo, G. P. Fagan, Ann. Drug 5 Data Rep. 15, 59, 1993), with anti-miciobial (A. G. Kamat, G. S. Gadaginamath, Indian J. Chem., Sect. B, 33, 255, 1994), with neuroleptic (J. Perregaard et al., J. Med. Chem. 35, 1092, 1.992), with anti-allergic (P. Ungast et al., J. Med. Chem. 32, 1360, 1989), with angiotensin-antagonistic (S. R. Stabler and Jahangir, Syn. Commun. 24, 123, 1994) and with PDGF receptor inhibitory action (Brian D. Palmer et al., J. Med. Chem. 41, 5457, 1998).

Compounds of the general formula I can be prepared according to various methods. A frequently used method consists in the reaction of aza-heterocycles with activated aryl halides in the presence of catalysts and/or bases or, in few cases, also without further additives, according to scheme 1:

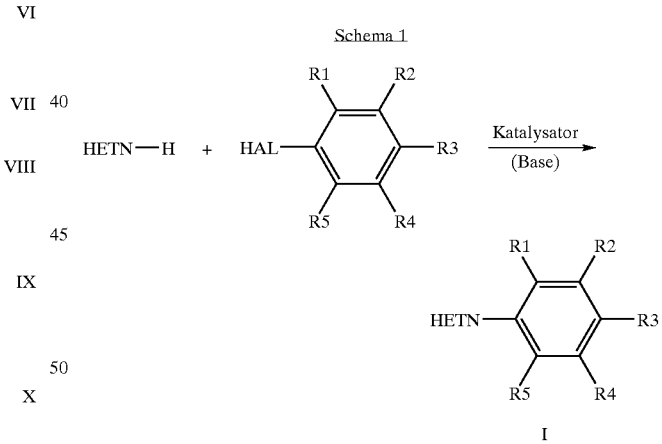

Thus, e.g. 1-(benzotriazol-1-yl)-2,4-dinitro-benzene can be obtained in 96% yield by 9 days boiling of benzotriazole in toluene (A. R. Katritzky, J. Wu, Synthesis 1994, 597).

4-Heterocyclicly-substituted nitrobenzenes and benzaldehydes can be obtained by reaction of the particular aza-heterocycles, such as e.g. benzotriazole, 1,2,4-triazole or benzimidazole, with 4-fluorobenzaldehyde or 4-fluoro- or 4-chlorobenzaldehyde in DMSO or DMF at 100° C. (D. J. Gale, J. F. K. Wilshire, Aust. J. Chem. 23, 1063, 1970; J. Rosevear, J. F. K. Wilshire, Aust. J. Chem. 44, 1097, 1991).

Nitrophenylazoles can be prepared by Ullmann condensation of azoles with aryl halides in pyridine in the presence of potassium carbonate and copper (II) oxide at high temperatures and long reaction times (M. A. Khan, J. B. Polys, J. Chem. Soc. (C), 1970, 85; A. K. Khan, E. K. Rocha, Chem. Pharm. Bull. 25, 3110, 1977) or, however, by reaction of azoles with suitable fluoronitrobenzenes in DMSO at comparatively high temperature and in the presence of potassium carbonate (M. F. Mackay, G. J. Trantino, J. F. Wilshire, Aust. J. Chem. 46, 417, 1993).

1-Arylindoles with activating substituents in the aryl part were obtained by reaction of indole with activated aryl halides in the presence of 37% $KF/Al_2O_3$ and catalytic amounts of crown ethers in DMSO at 120° C. (W. J. Smith, J. Scott Sawyer, Tetrahedron Lett. 37, 299, 1996).

There is also described the arylation of azoles with activated aryl halides in the presence of bases, such as caesium carbonate and sodium tert.-butylate, whereby, however, the presence of palladium catalysts is additionally necessary and the reaction itself requires high temperatures (65° to 120° C.) and long reaction times (3 to 48 hours) (G. Mann, J. F. Hartwig, M. D. Driver, C. Fernandez-Rivas, J. Am. Chem. Soc. 120, 827, 1998; I. P. Beletskaya, D. V. Davydov, M. MorenoManas, Tetrahedron Lett. 39, 5617, 1998).

The use of caesium carbonate as reagent in the case of carbon-heteroatom coupling reactions is also known but further special catalysts must additionally always be used in such reactions (Christopher G. Frost, Paul Mendonca, J. Chem. Soc., Perkin Trans. 1, 1998, 2615).

In general, from the above-given examples, it can be deduced that for arylations of azoles with activated aryl halides, relatively drastic conditions, such as high temperatures, long reaction times, as well as special catalysts, are frequently necessary.

In connection with the synthesis of a potentially anti-cancer compound, the reaction was investigated by use of morpholinopropanol (III) with o-nitrofluorobenzene (II) (scheme 2):

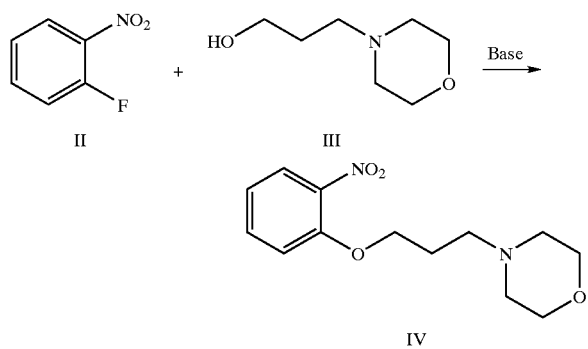

Based on our experience with the system caesium carbonate/dimethylformamide for the preparation of carbonates from alcohols and alkyl/aryl halides (DE 199 05 222.0) and of heterocyclic carbamates from aza-heterocycles and alkyl/aryl halides, we investigated whether this system is also suitable for the above reaction.

Surprisingly, it was found that this reaction leads at 23° C. within 48 hours to the desired product (IV) in 82% yield.

On the basis of this finding, it was now investigated whether other nucleophils, such as e.g. the nucleophils V to X also react with 2-fluoronitrobenzene at room temperature in the system caesium carbonate/dimethylformamide:

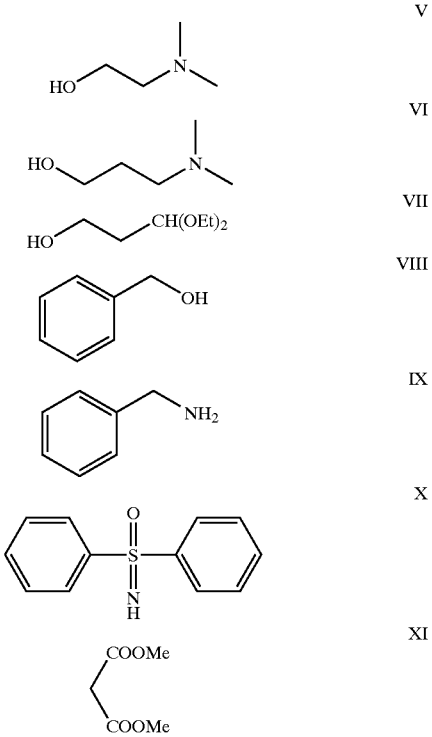

It was found that these reactions also give the desired products in good to very good yield at room temperature within 24 to 64 hours. The reaction of 2,5-difluoronitrobenzene (XII) with malonic acid dimethyl ester (XI) at room temperature in the system caesium carbonate/dimethylformamide also leads after 24 hours in 98% yield to the desired product XIII (scheme 3):

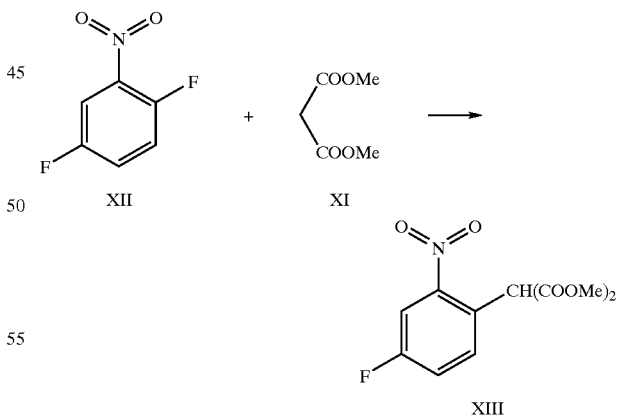

The preparation of compound XIII is described in the literature with use of sodium hydride in dimethyl sulphoxide at 100° C. in 96% yield (Li Sun et al., J. Med. Chem. 41, 2588, 1998).

Encouraged by these results, the arylation of aza-heterocycles with activated aromatics of the general formula XIV

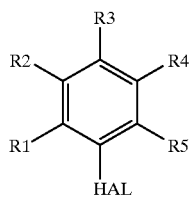

in which R[1] to R[5] have the above-given meaning and HAL stands for a halogen atom but especially for a fluorine atom, was investigated in the system caesium carbonate/dimethylformamide.

Surprisingly, it was found that almost all azaheterocycles used already react at room temperature in the presence of caesium carbonate/dimethylformamide with activated fluoroaromatics of the general formula XV to give compounds of the general formula I

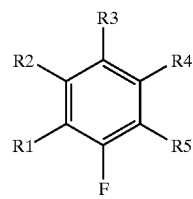

Instead of dimethylformamide, there can also be used other dipolar aprotic solvents, such as e.g. dimethylacetamide, acetonitrile, dimethylsulphoxide, acetone or N-methylpyrrolidone; however, the reaction times at room temperature are then distinctly longer and the yields often lower.

The process procedure in the case of the preparative carrying out of the arylation is very simple. One dissolves equimolar amounts of azaheterocycle and activated aromatics of the general formula XIV but especially of the general formula XV at room temperature in a suitable dipolar aprotic solvent, especially dimethylformamide, adds thereto a 2 to 4 molar excess of anhydrous caesium carbonate and stirs at room temperature until the reaction is ended. The reaction is monitored by means of thin layer chromatography. In the case of less reactive aromatics, in a few cases the reaction temperature must be increased to about 80° C.

At the end of the reaction, one pours the suspension on to water, extracts the product with ethyl acetate and purifies the product obtained after ev;~poration of the organic phase with the methods usual in organic chemistry, e.g. by crystallisation or chromatography.

The invention is illustrated and explained by the following embodimental examples:

EXAMPLE 1

2-Morpholinopropyloxynitrobenzene 0.57 g 2-fluoronitrobenzene, 0.65 g morpholinopropanol., 3.0 g caesium carbonate and 30 ml dimethylformamide are stirred for 2 days at room temperature in a closed 50 ml round-bottomed flask. One pours the suspension on to 50 ml water, extracts the aqueous phase 3 times with, in each case, 50 ml ethyl acetate and evaporates the combined organic phases on a rotavapor. For the removal of the dimethylformamide, which would disturb the chromatographic separation, the DMF-containing residue is again evaporated 2 to 3 times, together with some toluene, at 50° C. and 30 mbar vacuum. The oily residue is then purified on silica gel (0.04 to 0.063 mm) at 0.1 bar by flash chromatography. One obtains 0.9 g of oil (82.4%).

The following Examples were carried out analogously to Example 1, there are given the following reaction parameters (reaction time/eluent for chromatography/yield/physical statements):

EXAMPLE 2

2-Dimethylaminoethyloxynitrobenzene from 2-fluoronitrobenzene and 2-dimethylaminoethanol 64 h/toluene-ethanol 10+2/91.8%/oil

EXAMPLE 3

2-Dimethylaminopropyloxynitrobenzene from 2-fluoronitrobenzene and 3-dimethylaminopropanol-h/methylene chloride-methanol 10+2/58.7%/oil

EXAMPLE 4

2-(3,3-Diethoxypropoxy)-nitrobenzene from 2-fluoronitrobenzene and 3-hydroxypropionaldehyde diethyl acetal 64 h/hexane-ethyl acetate 10+2/83.7%/oil

EXAMPLE 5

2-Benzyloxynitrobenzene from 2-fluoronitrobenzene and benzyl alcohol 24 h/toluene/95.7%/oil

EXAMPLE 6

2-Benzylaminonitrobenzene from 2-fluoronitrobenzene and benzylamine 64 h/hexane-ethyl acetate 10+2/42.7%/m.p. 74° C.

EXAMPLE 7

4-Fluoro-2-nitrophenylmajonic acid dimethyl ester from 2,5-difluoronitrobenzene and malonic acid dimethyl ester 24 h/toluene-ethanol 10+0.5/98%/oil

EXAMPLE 8

N-2-Nitrophenyldiphenyl sulphoximide from 2-fluoronitrobenzene and diphenyl sulphoximide 48 h/toluene-ethanol 10+2/72%/m.p. 158° C.

EXAMPLE 9

N-2-cyanophenyldiphenyl sulphoximide from 2-fluorobenzonitrile and diphenyl sulphoximide at 80° C. 8 h/toluene-ethanol 10+1/74.3%/m.p. 160° C.

EXAMPLE 10

N-4-Cyanophenyldiphenyl sulphoximide from 4-fluorobenzonitrile and diphenyl sulphoximide 64 h/toluene-ethanol 10+1/61.2%/m.p. 159° C.

EXAMPLE 11

N-4-Nitrophenyldiphenyl sulphoximide from 4-fluoronitrobenzene and diphenyl sulphoximide 64 h/toluene-ethanol 10+0.5/64.1%/m.p. 166° C.

EXAMPLE 12

1-(2-Nitrophenyl)-indole from 2-fluoronitrobenzene and indole 24 h/hexane-ethyl acetate 10+2/90%/81° C.

EXAMPLE 13

1-(4-Cyanophenyl)-pyrrole from 4-fluorobenzonitrile and pyrrole at 80° C. 8 h/toluene/84.1%/105° C.

EXAMPLE 14

1-(4-Cyanophenyl)-pyrrole from 4-fluorobenzonitrile and pyrrole (room temperature) 64 h/toluene/toluene/39.1%/103–104° C.

EXAMPLE 15

1-(4-Cyanophenyl)-indole from 4-fluorobenzonitrile and indole 64 h/toluene-ethanol 10+1/100%/93–94° C.

EXAMPLE 16

1-(4-Ethoxycarbonylphenyl)-indole from 4-fluorobenzoic acid ethyl ester and indole at 80° C. 8 h/hexane-ethyl acetate 10+2/77.2%/m.p. 51° C.

EXAMPLE 17

1-(2-methoxycarbonylphenyl)-indole from 2-fluorobenzoic acid methyl ester and indole 64 h/toluene/20%/oil

EXAMPLE 18

1-(4-Nitrophenyl)-indole from 4-fluoronitrobenzene and indole 64 h/toluene/98%/m.p. 134° C.

EXAMPLE 19

1-(2-Nitrophenyl)-indole-5-carboxylic acid methyl ester from 2-fluoronitrobenzene and indole-5-carboxylic acid methyl ester 64 h/toluene-ethanol 10+1/98%/m.p. 89° C.

EXAMPLE 20

1-(2-nitrophenyl)-indole-3-carboxylic acid methyl ester from 2-fluoronitrobenzene and indole-carboxylic acid methyl ester 24 h/toluene-ethanol 10+1/96%/m.p. 155° C.

EXAMPLE 21

1-(2-Nitrophenyl)-indole-3-carbonitrile from 2-fluoronitrobenzene and indole-3-carbonitrile 24 h/toluene-ethanol 10+1/98%/m.p. 151° C.

EXAMPLE 22

1-(Benzotriazol-1-yl)-2,4-dinitrobenzene from fluoro-2,4-dinitrobenzene and benzotriazole 24 h/toluene-ethanol 10+1/85.5%/m.p. 185° C.

EXAMPLE 23

1-(Benzotriazol-1-yl)-2,4-dinitrobenzene from chloro-2,4-dinitrobenzene and benzotriazole 24 h/toluene-ethanol 10+1/85.5%/m.p. 185° C.

EXAMPLE 24

1-(4-Nitrophenyl)-indole-3-aldehyde from 4-fluoronitrobenzene and indole-3-aldehyde 24 h/crystallisation in the case of working up/91.6%/m.p. 269° C.

EXAMPLE 25

1-(4-Formylphenyl)-indole from 4-fluorobenzaldehyde and indole 48 h/toluene/7.7%/oil

EXAMPLE 26

1-(2-Methoxycarbonylphenyl)-indole from 2-fluorobenzoic acid methyl ester and indole at 80° C. 8 h/hexane-ethyl acetate 10+2/19.4%/oil

EXAMPLE 27

5-Methyl-1-(4-nitrophenyl)-indole from 4-fluoronitrobenzene and 5-methylindole 24 h/toluene/77.3%/m.p. 147° C.

EXAMPLE 28

5-Nitro-1-(4-nitrophenyl)-indole from 4-fluoronitrobenzene and 5-nitroindole 24 h/crystallisation in the case of working up/86.9%/m.p. 235° C.

EXAMPLE 29

5-Chloro-1-(2-nitrophenyl)-indole from 2-fluoronitrobenzene and 5-chloroindole 24 h/toluene/71.5%/m.p. 142° C.

EXAMPLE 30

5-Methoxy-L-(2-cyanophenyl)-indole from 2-fluorobenzonitrile and 5-methoxyindole 3 h/toluene/100%/m.p. 99° C.

EXAMPLE 31

1-(2-Nitrophenyl)-pyrrole from 2-fluoronitrobenzene and pyrrole 64 h/hexane-ethyl acetate 10+2/68.6%/m.p. 105° C.

EXAMPLE 32

5-Methoxy-1-(4-nitrophenyl)-indole from 4-chloronitrobenzene and 5-methoxyindole at 80° C. 8 h/toluene/27.2%/m.p. 187° C.

EXAMPLE 33

3-Methyl-1-(4-nitrophenyl)-indole from 4-fluoronitrobenzene and 3-methylindole 24 h/toluene/84.1%/m.p. 146° C.

EXAMPLE 34

5-Methoxy-1-(4-ethoxycarbonylphenyl)-indole from 4-fluorobenzoic acid ethyl ester and 5-methoxyindole at 80° C. 8 h/hexane-ethyl acetate 10+2/68.5%/oil

EXAMPLE 35

5-Methoxy-1-(4-nitrophenyl)-indole from 4-fluoronitrobenzene and 5-methoxyindole 18 h/crystallisation in the case of working up/88.1%/5 m.p. 188° C.

EXAMPLE 36

1-(2-Nitrophenyl)-indole-2-carboxylic acid ethyl ester from 2-fluoronitrobenzene and indole-2-carboxylic acid ethyl ester 58 h/toluene/47.9%/m.p. 90° C.

EXAMPLE 37

1-(4-Nitrophenyl)-indole-2-carboxylic acid ethyl ester from 4-fluoronitrobenzene and indole-2-carboxylic acid ethyl ester at 80° C. 8 h/toluene/78.5%/m.p. 135° C.

EXAMPLE 38

1-(3-Nitrophenyl)-indole from 3-fluoronitrobenzene and indole at 80° C. 6 h/hexane-ethyl acetate 10+2/72.9%/m.p. 66° C.

EXAMPLE 39

1-(3-Cyanophenyl)-indole from 3-fluorobenzonitrile and indole at 80° C. 8 h/toluene-ethanol 10+1/55.8%/m.p. 37° C.

EXAMPLE 40

1-(2-Cyanophenyl)-indole from 2-fluorobenzonitrile and indole 64 h/toluene/100%/m.p. 112° C.

EXAMPLE 41

1-(2-Nitrophenyl)-imidazole from 2-fluoronitrobenzene and imidazole 18 h/toluene-ethanol 10+2/92%/m.p. 98°–99° C.

EXAMPLE 42

1-(2-Nitrophenyl)-benzimidazole from 2-fluoronitrobenzene and benzimidazole 18 h/toluene-ethanol 10+2/98.8%/oil

EXAMPLE 43

1-(4-Nitrophenyl)-indazole from 4-fluoronitrobenzene and indazole 18 h/crystallisation in the case of working up/92%/m.p. 166° C.

EXAMPLE 44

N-2,4-Dibitrophenylcarbazole from 2,4-dinitrofluorobenzene and carbazole 18 h/crystallisation in the case of working up/m.p. 189° C.

EXAMPLE 45

1-(2-Cyanophenyl)-1,2,3-triazole from 2-fluorobenzonitrile and 1,2,3-triazole 24 h/toluene-ethanol 10+1/14.2%/m.p. 112° C.

EXAMPLE 46

4-(4-Cyanophenyl)-1,2,4-triazole from 4-fluorobenzonitrile and 1,2,4-triazole 24 h/toluene-ethanol 10+2/14.2%/m.p. 169° C.

EXAMPLE 47

5-Chloro-1-(2-cyanophenyl)-indole from 2-fluorobenzonitrile and 5-chloroindole 2 h/toluene/70.4%/m.p. 129–130° C.

EXAMPLE 48

1-(2-Pyridyl)-indole from 2-fluoropyridine and indole at 80° C. 24 h/toluene/84.1%/m.p. 58° C.

What is claimed is:
1. A process for preparing compounds of general formula I,

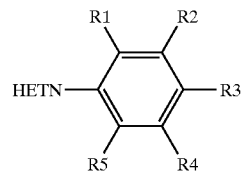

in which HETN is an indol-1-yl and R1, R2, R3, R4, and R5 are independently hydrogen, nitro, cyano, alkoxycarbonyl with up to 5 carbon atoms, aldehyde, alkylcarbonyl with up to 5 carbon atoms, arylcarbonyl, or amide, provided that R1, R2, R3, R4, and R5 are not all hydrogen atoms, the process comprising:

reacting an aromatic aza-heterocycle with a compound of general formula XIV,

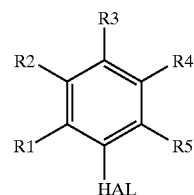

wherein HAL is halogen, and R1, R2, R3, R4, and R5 are as defined above, at a temperature between room temperature and about 80° C., inclusive, and in the presence of cesium carbonate and one or more dipolar aprotic solvents, wherein the aromatic aza-heterocycle is an indole.

2. The process according to claim 1, wherein the solvent is acetone, acetonitrile, dimethylsulphoxide, dimethylacetamide, N-methylpyrrolidone or dimethylformamide.

3. The process according to claim 1, wherein the solvent is dimethylformamide.

4. The process according to claim 1, wherein HAL in general formula XIV is a fluorine atom.

5. The process according to claim 1, wherein the aromatic aza-heterocycle and the compound of general formula XIV are reacted at room temperature.

* * * * *